(12) United States Patent
Hartfield

(10) Patent No.: US 8,513,622 B2
(45) Date of Patent: Aug. 20, 2013

(54) METHOD FOR EXTRACTING FROZEN SPECIMENS AND MANUFACTURE OF SPECIMEN ASSEMBLIES

(75) Inventor: Cheryl Hartfield, Dallas, TX (US)

(73) Assignee: Omniprobe, Inc., Dallas, TX (US)

( * ) Notice: Subject to any disclaimer, the term of this patent is extended or adjusted under 35 U.S.C. 154(b) by 17 days.

(21) Appl. No.: 13/439,346

(22) Filed: Apr. 4, 2012

(65) Prior Publication Data

US 2013/0091875 A1    Apr. 18, 2013

Related U.S. Application Data

(60) Provisional application No. 61/471,425, filed on Apr. 4, 2011.

(51) Int. Cl.
| | | |
|---|---|---|
| *G01N 3/18* | (2006.01) | |
| *G01N 1/42* | (2006.01) | |
| *B01L 7/00* | (2006.01) | |

(52) U.S. Cl.
USPC .............. 250/440.11; 250/442.11; 250/443.1; 73/864.91; 73/863.12; 427/551; 62/62

(58) Field of Classification Search
USPC ............ 250/440.11, 442.11, 443.1; 427/551; 73/864.91, 863.12; 62/62
See application file for complete search history.

(56) References Cited

U.S. PATENT DOCUMENTS

| | | | |
|---|---|---|---|
| 6,781,125 B2 | 8/2004 | Tokuda et al. | |
| 7,435,353 B2 | 10/2008 | Golovchenko et al. | |
| 7,845,245 B2* | 12/2010 | Hayles et al. | 73/864.91 |
| 2007/0184515 A1* | 8/2007 | Goodman et al. | 435/40.5 |
| 2010/0089516 A1 | 4/2010 | Kawamoto | |
| 2012/0003394 A1* | 1/2012 | Mulders et al. | 427/551 |

FOREIGN PATENT DOCUMENTS

| | | |
|---|---|---|
| EP | 2402475 A1 | 4/2012 |
| JP | 2002214091 A | 7/2002 |

OTHER PUBLICATIONS

International Searching Authority, International Application No. PCT/US2012/032141, International Search Report and the Written Opinion, Nov. 29, 2012.

* cited by examiner

*Primary Examiner* — Nikita Wells
(74) *Attorney, Agent, or Firm* — John A. Thomas

(57) ABSTRACT

A method for attaching a frozen specimen to a manipulator probe tip typically inside a charged-particle beam microscope. The method comprises cooling the probe tip to a temperature at or below that of the frozen specimen, where the temperature of the frozen specimen is preferably at or below the vitrification temperature of water; bringing the probe tip into contact with the frozen specimen, and bonding the probe tip to the frozen specimen by flowing water vapor onto the region of contact between the probe tip and the frozen specimen. The bonded probe tip and specimen may be moved to a support structure such as a TEM grid and bonded to it by similar means. The probe tip can then be disconnected by heating the probe tip or applying a charged-particle beam.

36 Claims, 3 Drawing Sheets

METHOD FOR EXTRACTING FROZEN SPECIMENS AND MANUFACTURE OF SPECIMEN ASSEMBLIES

CLAIM FOR PRIORITY

This application claims the priority of U.S. Provisional Patent Application Ser. No. 61/471,425, titled "METHOD FOR EXTRACTING FROZEN SPECIMENS AND MANUFACTURE OF SPECIMEN ASSEMBLIES," and filed Apr. 4, 2011, which is incorporated in its entirety by reference into the present application.

BACKGROUND

1. Technical Field

This disclosure relates to methods and apparatus for extracting a specimen from a sample substrate at cryogenic temperature for analysis, in particular, methods and apparatus for such extraction inside a charged-particle instrument such as a focused ion-beam microscope (FIB) or scanning electron microscope (SEM).

2. Background Art

While FIB processes have been used in semiconductor and materials science since the 1990's, they are only recently being used by the biological community. Biological samples are generally either embedded in polymeric material such as Epon, or frozen, before sectioning for microscopic imaging. While polymeric-embedded specimens can easily be prepared using the traditional in situ lift-out steps and materials, the lift-out process must be modified to meet requirements related to the frozen specimen.

It is known that traditional gas-assisted ion and electron deposition processes are not viable solutions for bonding the specimen to other objects, such as probe tips or sample holders, at very cold temperatures, since the metallo-organic precursors tend to uncontrollably condense on the specimen in their native precursor form, which results in a suboptimal masking layer for protection of the specimen's top surface during FIB milling. Temperature manipulation can be used, however, to achieve bonding without using gas-assisted deposition. Modifying or maintaining the temperature of frozen biological specimens within the electron microscope is common during manipulation, imaging and analysis of these frozen specimens. To preserve the morphological integrity of a frozen biological specimen during cryo-FIB and cryo-handling methods, however, the specimen temperature in the region of interest should preferably not rise above the vitrification temperature for water, approximately −140° C. Otherwise, ice crystals form within the specimen and damage its structure. Ice-crystal frost must also be avoided for quality imaging and processing of the specimen.

Existing nano-manipulators typically have a moveable probe carrying a fine probe tip. U.S. Pat. No. 7,845,245 (which is not admitted to be prior art by its inclusion in this background section) describes touching a warm probe tip to a vitrified biological specimen, to achieve bonding of the tip to the specimen, based on local induction of a phase change.

This phase change causes the resulting bonding, but also may induce the formation of ice crystals as the sample is warmed above its vitrification temperature at the attachment site. What is needed is a way to create a secure bond of a specimen to a probe tip or other end effector without the risk of devitrification and formation of ice crystals inside the specimen or the formation of frost on the outside of the specimen.

DRAWINGS

DESCRIPTION

This application uses the term "FIB" or "charged-particle instrument" generically for any kind of instrument using one or more radiation beams to assist chemical vapor-deposition procedures, etch, or lift-out of specimens in a vacuum. These terms as used here thus include instruments using ion beams, electron beams, other charged-particle beams, or light energy, such as a beam of laser light, or any combination of these beams. The term "cryogenic" as used here refers to cold temperatures, generally below zero degrees C., that result in freezing of the sample or condensing of a chemical vapor, including, but not limited to, water vapor. Unless otherwise stated, the terms "probe tip" or "tip" refer to any part of a manipulator apparatus intended to be bonded to a specimen for lift-out and manipulation. A suitable nano-manipulator system is the AutoProbe Model 300, manufactured by Omniprobe, Inc. of Dallas, Tex. In the Omniprobe apparatus, the probe tip is usually a fine tungsten needle.

Figure 1:
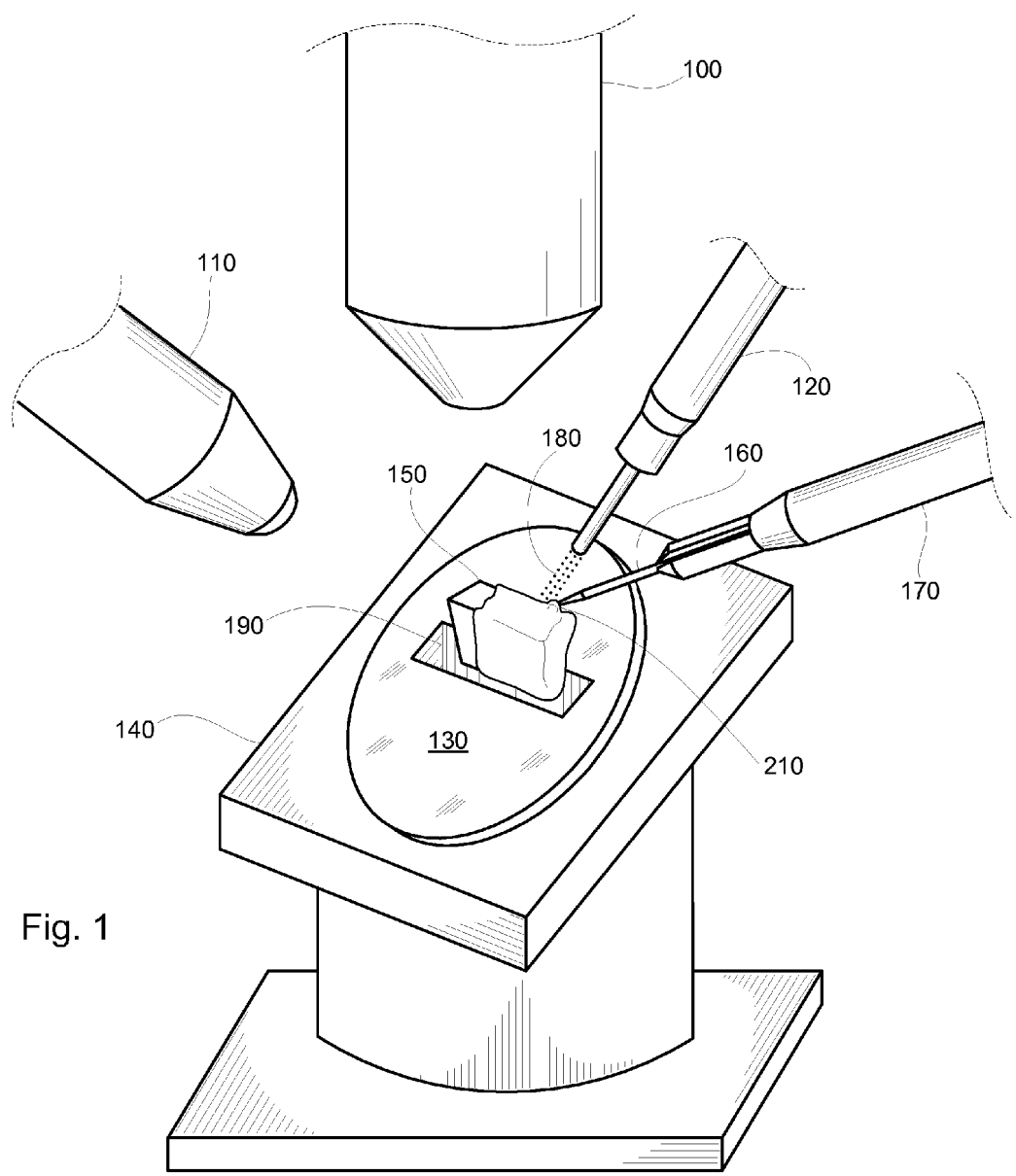
FIG. 1 shows an exemplary embodiment of my method for controlled vapor attachment of a specimen that has been wholly or partly excised from a larger frozen sample inside a FIB instrument, where the probe tip is initially placed in contact with the specimen.

FIG. 1 is a schematic drawing of a FIB instrument having an electron beam column (100), and ion beam column (110) and a gas-injection system (120). A bulk sample (130) is shown located on a cold stage (140). FIG. 1 further shows a specimen (150) that has been excised from the bulk sample (130), for example by milling with the ion beam (110). The specimen (150) is shown in the process of being attached to the probe tip (160) of a nano-manipulator (170) by deposition of water vapor (180) from the gas injection system (120) to form a condensing layer.

Water vapor is a preferred condensate due to its low cost, wide availability and ability to condense as an amorphous layer under high vacuum conditions of about 10-6 mbar at temperatures compatible with the requirements of preserving the structure of vitrified biological specimens. Other condensate species than water may be used, as long as the conversion from vapor to solid phase occurs at a temperature that will not negatively impact the sample and results in a condensate with acceptable topography and stability. Pressure and temperature combinations can be determined for other condensate species. Examples of other species that may form suitable condensates include inert gases such as argon or xenon, alcohols, and methanes. These may be used alone or mixed with water at a suitable ratio to allow a condensate species that forms an amorphous layer in a desired temperature range. For example, a 50% methanol/water solution (by volume) freezes at about −40° C. and 100% methanol freezes at about −100° C. For applications using water vapor, it may be preferable to use temperatures at about −93° C. or less, and more preferably at about less than −140° C., to reduce the sublimation may occur at warmer temperatures.

Water vapor (180) can be supplied to the specimen (150) from, e.g., liquid water, heated Epsom salts or sulfates, or other high vapor pressure solids that can vaporize. The injector (120) to the chamber can here be a simple leak valve, a mass flow controller, or other suitable injector. Given that the injector may include a tube nozzle that produces directional vapor injection, a highly controllable valve or other controller is preferred along with a diffuser or other device for enabling diffusivity of vapor (180) introduction to the chamber. A suitable gas-injection system (120) for precise control of the vapor stream is the OmniGIS, manufactured by Omniprobe, Inc.

The relative sizes of the specimen (150), and the trench (190) from which it was cut have been greatly exaggerated in the figures for clarity. A typical specimen to be prepared for TEM examination, for example, would be about 10-20 μm across and 5-10 μm deep.

By keeping both the tip and specimen at substantially the same cold temperature, bonding can be achieved by directing vapor (180) to the exposed joining region (210) where the probe tip (160) contacts, or nearly contacts, the specimen (150). At an optimized injection distance and flux, the vapor (180) will condense and freeze in a conformal thin layer, building up with continued supply of vapor, thus joining the specimen (150) to the manipulator tip (160) without depositing an uneven, rough or thick obscuring layer on the region of interest of the specimen (150).

First, the specimen (150) is cooled below the vitrification temperature and mounted inside the FIB. Typically this mount would include a conventional cryogenic stage (140).

The specimen temperature may be regulated based on the solid condensate species selected and on the type of specimen (as non-biological specimens may not require vitrification temperatures). With water vapor, for example, the specimen temperature is held below a temperature at which the water vapor condenses to form a solid ice condensate layer. For many applications, it can be preferred to maintain the specimen temperature at about 90 degrees C. or less, and more preferably to maintain the specimen temperature at about 140 degrees C. or less to enable formation of a uniform, smooth, amorphous and conformal solid ice condensate layer. This type of layer allows subsequent FIB milling of the sample without inducing curtaining artifacts. Temperatures above $-140°$ C. can be used when the morphology of the solid ice condensate layer is acceptable and where no damage or artifacts are introduced to the sample.

The probe tip (160) is cooled to a temperature substantially equal to that of the specimen (150), but below the devitrification temperature. (Note that cooling below the devitrification temperature may not be required for some non-biological specimens.) The probe tip (160) can be actively cooled, by, for example, directing a flow of cooled non-reactive gas upon it, such as nitrogen, or using a cooling wire to form a high thermal conductivity path to a cooling block kept cold by liquid nitrogen or the like. Alternatively, the probe tip (160) can be passively cooled by touching the probe tip (160) down on the cryo-stage (140) and holding for a sufficient time to bring the temperature of the tip (160) to that of the specimen (150).

The optimum temperature of the probe-tip (160) can be found experimentally by trying different cold-soaking times followed by touching the probe tip (160) to the sample substrate (130) or to some sacrificial region on the specimen (150). No bonding should occur if both are substantially the same temperature, and once established, the soaking time should be reasonably consistent between different specimens (150) of the same material.

Touching on the cryo-stage (140) or another cryo object is preferred to touching on the specimen (150), because the warmer tip (160) will sublimate a biological specimen (150). The specimen (150) will then freeze back to the tip (160) as both reach thermal equilibrium. The methods claimed here avoid the phase change and the likely formation of ice crystals that may occur with a touch-down on the specimen (150) with a warmer probe tip (160). Ice crystals inside the specimen (150) will disrupt cellular specimens; frost on the outside of the specimen (150) will not damage the internals of the specimen (150), but will interfere with imaging. Both cases should be avoided. Frost on the outside of a specimen (150) may be controlled by a conventional cold finger (not shown) inside the FIB chamber.

We then move the temperature-adjusted probe tip (160) into proximity with the surface of the specimen (150). It may hovers slightly above the specimen, or make contact either directly on the specimen (150), or on an optional protective layer (200) previously laid down on the specimen (150). The protective layer (200) may or may not sublimate upon contact, depending on the protective-layer material (200). A typical material for such a protective layer (200) for biological samples would be water vapor (180), forming ice, or other condensing substances as noted above.

FIG. 1 shows the case where the probe tip is in contact with the specimen (150). As shown in the figures, vapor (180) is then flowed over the specimen (150), including the joining region (210) either during the tip (160) approach or after contact is made with the specimen (150). If desired, the injector (120) needle can be positioned about 5 mm or greater from the specimen (150) to avoid point-source shadowing or non-conformal coating.

During these joining processes, a non-condensing cooled gas, such as nitrogen, can also be flowed onto the joining region (210) to help maintain the probe tip (160) and the specimen (150) at the same temperature and avoid frost formation. Preferably, the area of the specimen (150) impacted by the water vapor (180) should be limited to the area immediately around the probe tip (160), so that ice does not form over the specimen (150) generally, but depending on the method or the apparatus used to apply water vapor (180), a larger area of the specimen (150) may end up coated with an ice layer, as shown in FIG. 1. Preferably, the water vapor (180) is delivered in pulses, or at a controlled flow rate, so that the bonding ice region (210) is built up in several layers at a rate approximately no greater than about 25 nm per second.

The joining process is completed when it is confirmed that the probe tip (160) can be lifted, with the specimen (150) staying joined and lifting out also.

Figure 2:
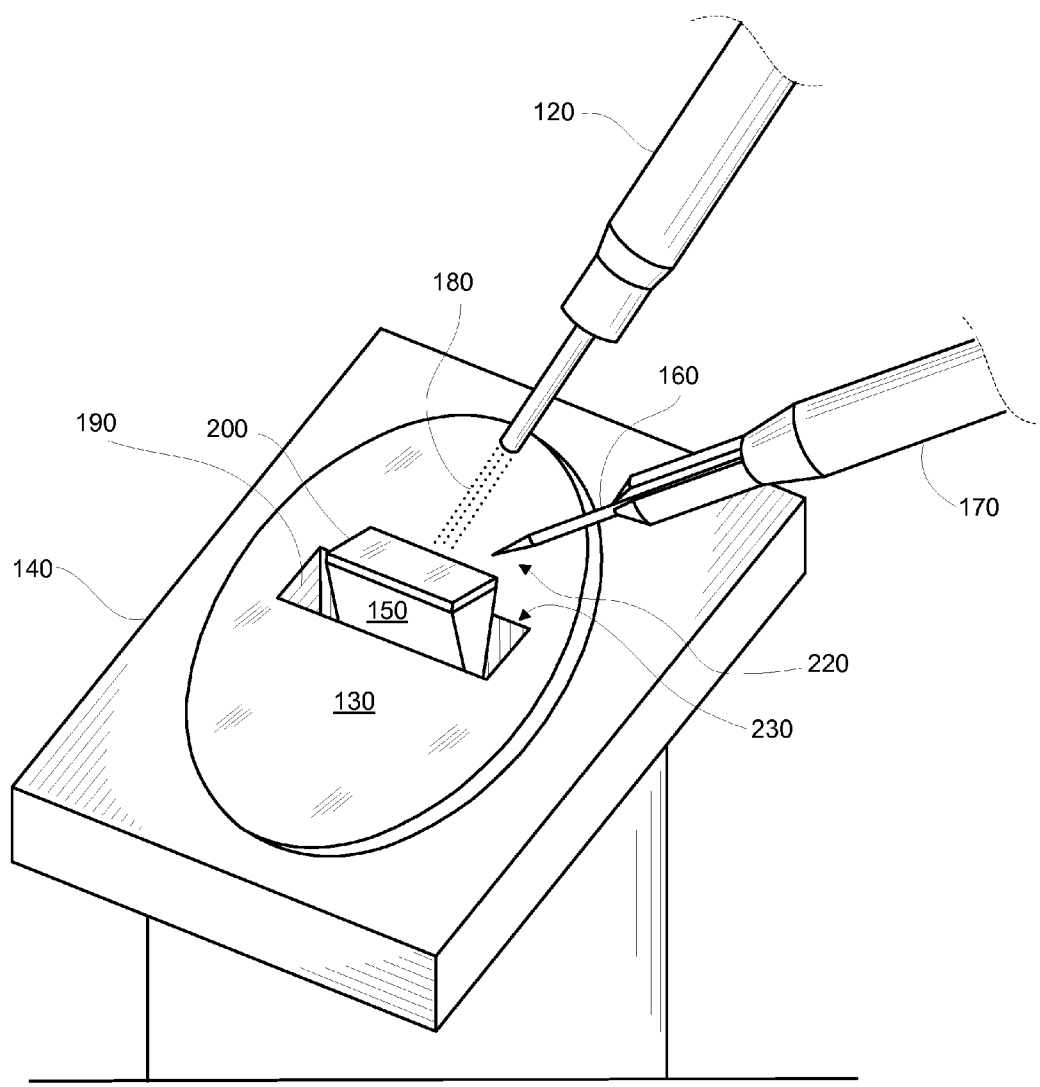
FIG. 2 shows another embodiment of my method for controlled-vapor attachment, where a gap initially exists between the probe tip and the specimen.

In another embodiment, shown in FIG. 2, the probe tip (160) is moved close to the specimen (150), but remains separated from the specimen by a first gap (220) sufficiently small to allow bonding of the tip (160) to the specimen (150) by the water vapor (180), as discussed above. In either embodiment it is preferable to keep the first gap (220) between the probe tip (160) and the specimen (150) smaller than the second gap (230) between the specimen (150) and any substrate or bulk sample (130) from which it has been excised, so that a bonding ice film (210) is not at the same time created at the second gap (230) between the specimen (150) and substrate (130). This consideration may not be relevant for a gas-injection apparatus where the region of water-vapor or gas impact can be precisely controlled, but such precise control is not possible with all gas-injection apparatus available today.

In another embodiment, certain specimens may be manipulated at cold temperatures above the vitrification temperature of water. Materials not containing water, such as indium nitride are candidates for such manipulation. Indium nitride for example requires manipulation at cryogenic temperatures because the gallium ions from the ion beam react with it, and its structure will not be preserved unless the preparation is done at cryogenic temperatures. Since the Ga ions are implanted, if the specimen is warmed up after milling the reaction will still take place. So, both milling and lift-out should be done at low temperatures. Temperatures below the vitrification point of water, however, are not necessary, so long as the temperature is sufficiently low to maintain the structure of interest and result in a condensate with acceptable topography and stability. For some materials, even temperatures slightly below zero degrees C. may be protective. Some materials may not require any cooling to preserve their structure during FIB processing. In this case, cryogenic temperature is required only to enable the bonding process as described above.

Figure 3:
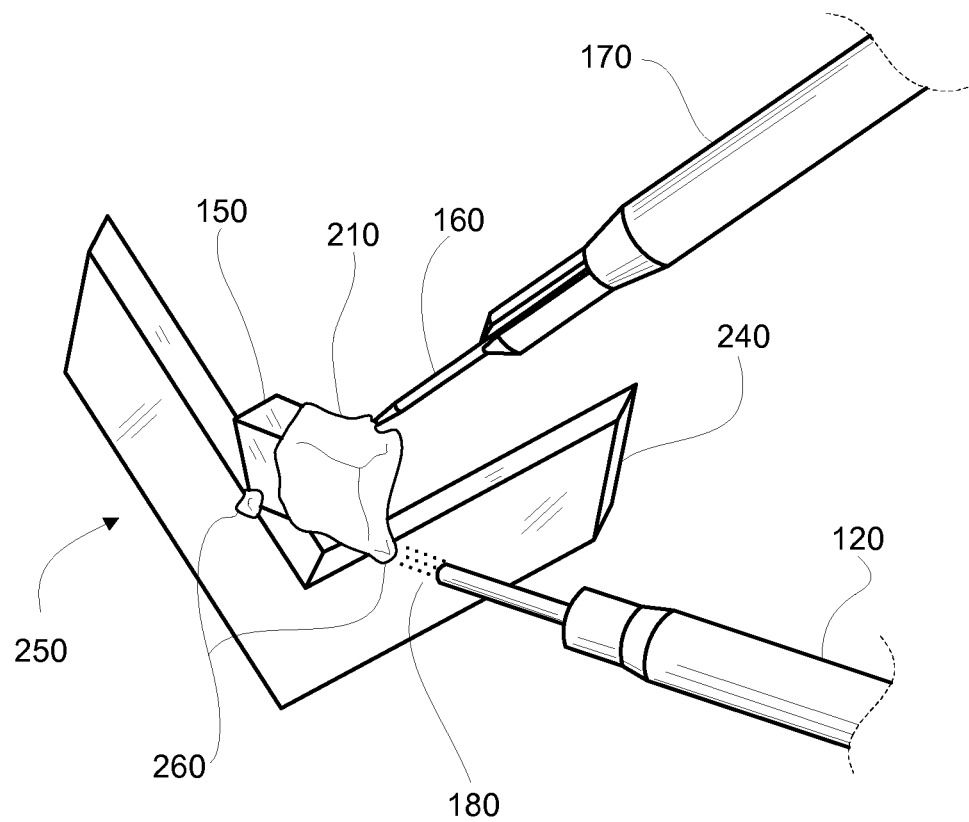
FIG. 3 shows an exemplary specimen attached to a probe tip that has been lifted out of a frozen sample and positioned to be bonded to a TEM grid by the methods claimed.

The processes disclosed and claimed here may be used to construct a specimen assembly (250) comprising a probe tip (160), the frozen specimen (150), at least one joining region (210) of ice and a support structure (240). The technique can be used for any type of joining of a frozen specimen (150) to objects other than probe tips (160), such as a transmission-electron microscope (TEM) grid or holder (240), as shown in FIG. 3. Because the ice coating left by the water vapor deposition is relatively thin, it is easy to separate any specimens (150) from the probe tip (160) by FIB or electron beam cutting, for example, leaving the specimen (150) bonded to another object, such as the TEM grid (240) shown in FIG. 3, where the specimen (150) is bonded to the TEM grid (240) by regions (260) of ice deposition.

As shown in FIG. 3, the excised specimen (150) is positioned in contact, or nearly in contact, with a cryo-cooled structure (240), in this case a TEM grid, and vapor (180) is flowed onto the areas chosen for bonding to create one or more regions (260) of ice deposition, generally as previously described for the creation of ice joining regions (210).

None of the description in this application should be read as implying that any particular element, step, or function is an essential element which must be included in the claim scope; the scope of patented subject matter is defined only by the allowed claims. Moreover, none of these claims are intended to invoke paragraph six of 35 U.S.C. Section 112 unless the exact words "means for" are used, followed by a gerund. The claims as filed are intended to be as comprehensive as possible, and no subject matter is intentionally relinquished, dedicated, or abandoned.

I claim:

1. A method for attaching a frozen specimen to a probe tip; the method comprising:
    cooling the probe tip to a temperature at or below that of the frozen specimen,
        where the temperature of the frozen specimen is at or below zero degrees C.;
    bringing the probe tip into contact with the frozen specimen; and,
    bonding the probe tip to the frozen specimen by flowing vapor onto the region of contact between the probe tip and the frozen specimen.

2. The method of claim 1 where the method is performed in a vacuum and the vapor is water vapor.

3. A method for attaching a frozen specimen to a probe tip; the method comprising:
    cooling the probe tip to a temperature at or below that of the frozen specimen,
        where the temperature of the frozen specimen is at or below zero degrees C.;
    bringing the probe tip close to the frozen specimen and leaving a first gap between the probe tip and the specimen;
    bonding the probe tip to the frozen specimen by flowing vapor onto the first gap between the probe tip and the frozen specimen.

4. The method of claim 3 where the method is performed in a vacuum and the vapor is water vapor.

5. A method for attaching a frozen specimen to a probe tip; the method comprising:
    cooling the probe tip to a temperature at or below that of the frozen specimen,
        where the temperature of the frozen specimen is at or below the vitrification temperature of water;
    bringing the probe tip into contact with the frozen specimen; and,
    bonding the probe tip to the frozen specimen by flowing water vapor onto the region of contact between the probe tip and the frozen specimen.

6. The method of claim 5 where the method is performed in a vacuum.

7. A method for attaching a frozen specimen to a probe tip; the method comprising:
    cooling the probe tip to a temperature at or below that of the frozen specimen,
        where the temperature of the frozen specimen is at or below the vitrification temperature of water;
    bringing the probe tip close to the frozen specimen and leaving a first gap between the probe tip and the specimen;
    bonding the probe tip to the frozen specimen by flowing water vapor onto the first gap between the probe tip and the frozen specimen.

8. The method of claim 7 where the method is performed in a vacuum.

9. The method of claim 7, where there is a second gap between the frozen specimen and a bulk sample from which the specimen was extracted; the method further comprising:
    maintaining the first gap smaller than the second gap while flowing water vapor onto the first gap.

10. A method for making a frozen specimen assembly; the method comprising:
    cooling an object to a temperature at or below that of a frozen specimen,
        where the temperature of the frozen specimen is at or below the vitrification temperature of water;
    bringing the object into contact with the frozen specimen;
    bonding the object to the frozen specimen by flowing water vapor onto the region of contact between the object and the frozen specimen;
    moving the object and the frozen specimen bonded thereto to a support structure;
    bonding the frozen specimen to the support structure by flowing water vapor onto one or more regions of contact between the support structure and the frozen specimen; and,
    freeing the object from the frozen specimen.

11. The method of claim 10 where the method is performed in a vacuum.

12. The method of claim 10, where the object is a nanomanipulator probe tip.

13. The method of claim 10, where the object is a TEM grid.

14. The method of claim 10, where the freeing of the object from the frozen specimen is accomplished by heating the object.

15. The method of claim 10 where the freeing of the object from the frozen specimen is accomplished by application of a charged-particle beam.

16. A method for making a frozen specimen assembly; the method comprising:
cooling an object to a temperature at or below that of a frozen specimen,
where the temperature of the frozen specimen is at or below zero degrees C.;
bringing the object into contact with the frozen specimen;
bonding the object to the frozen specimen by flowing water vapor onto the region of contact between the object and the frozen specimen;
moving the object and the frozen specimen bonded thereto to a support structure;
bonding the frozen specimen to the support structure by flowing water vapor onto one or more regions of contact between the support structure and the frozen specimen;
and,
freeing the object from the frozen specimen.

17. The method of claim 16 where the method is performed in a vacuum.

18. The method of claim 16, where the object is a nano-manipulator probe tip.

19. The method of claim 16, where the object is a TEM grid.

20. The method of claim 16, where the freeing of the object from the frozen specimen is accomplished by heating the object.

21. The method of claim 16 where the freeing of the object from the frozen specimen is accomplished by application of a charged-particle beam.

22. A frozen specimen assembly; the frozen specimen assembly constructed according to the method of claim 10.

23. A frozen specimen assembly; the frozen specimen assembly constructed according to the method of claim 11.

24. A frozen specimen assembly; the frozen specimen assembly constructed according to the method of claim 12.

25. A frozen specimen assembly; the frozen specimen assembly constructed according to the method of claim 13.

26. A frozen specimen assembly; the frozen specimen assembly constructed according to the method of claim 14.

27. A frozen specimen assembly; the frozen specimen assembly constructed according to the method of claim 15.

28. A frozen specimen assembly; the frozen specimen assembly constructed according to the method of claim 16.

29. A frozen specimen assembly; the frozen specimen assembly constructed according to the method of claim 17.

30. A frozen specimen assembly; the frozen specimen assembly constructed according to the method of claim 18.

31. A frozen specimen assembly; the frozen specimen assembly constructed according to the method of claim 19.

32. A frozen specimen assembly; the frozen specimen assembly constructed according to the method of claim 20.

33. A frozen specimen assembly; the frozen specimen assembly constructed according to the method of claim 21.

34. An apparatus for forming specimen assemblies from a frozen sample, the apparatus comprising:
a stage for holding a sample; the stage equipped to position a region of interest in the sample, where at least the part of the stage in contact with the sample can be cooled to a cryogenic temperature;
a manipulator; the manipulator having a probe tip; the probe tip equipped to be held at a cryogenic temperature;
a source of water vapor capable of being delivered substantially to the region of interest in the sample;
wherein
the probe tip can be held at a cryogenic temperature when the probe tip is in contact with a specimen comprising the region of interest, and when water vapor is flowed over the probe tip and at least a portion of the specimen.

35. The apparatus of claim 34, further comprising a source of heat sufficient to raise the temperature of the probe tip above a cryogenic temperature and selectively release the probe tip from the region of interest.

36. The apparatus of claim 34 where the source of heat is a charged-particle beam.

* * * * *